United States Patent [19]
Nakamura et al.

[11] Patent Number: 5,922,599
[45] Date of Patent: Jul. 13, 1999

[54] METHOD FOR LARGE-SCALE PROPAGATION OF TREES OF GENUS GMELINA BY TISSUE CULTURE

[75] Inventors: Kentaro Nakamura; Ryo Soda, both of Tsukuba, Japan

[73] Assignee: Sumitomo Forestry Co., Ltd., Osaka, Japan

[21] Appl. No.: 08/810,670

[22] Filed: Mar. 3, 1997

[51] Int. Cl.$^6$ .................................................. C12N 5/00
[52] U.S. Cl. ........................... 435/430; 435/410; 435/420
[58] Field of Search .................... 435/410, 420, 435/430, 431; 47/17, DIG. 3

[56] References Cited

PUBLICATIONS

Murashige, T. and Skoog, F., "A Revised Medium for Rapid Growth and Bio Assays with Tobacco Tissue Cultures," *Physiolgia Plantarum*, vol. 15, 1962, pp. 473–497.
Gamborg, O.L., et al., "Nutrient Requirements of Suspension Cultures of Soybean Root Cells," *Experimental Cell Research*, vol. 50, 1968, pp. 151–158.
Yang et al., Micropropagation of Gmelina Aborea R., Proceedings of the SABRAO International Symposium 29, 1992, pp. 213–218.
Crizaldo, Tissue Culture Of Fast–Growing Trees, Sylvatrop Philipp. For. Res. J. 5(2): (1980) pp. 123–137.
SK Roy et al (1992) In Vitro Cellular & Developmental Biology 28(3, pt. II): 116A.
HT Hartmann et al (1975) Plant Propagation Principles and Practices pp. 17–52.
SH Mantell et al (1985) Principles of Plant Biotechnology pp. 130–157, 227, 230.

*Primary Examiner*—Bruce R. Campell
*Attorney, Agent, or Firm*—Pollock, Vande Sande & Amernick

[57] ABSTRACT

Plantlets of trees of genus Gmelina can be efficiently regenerated on a large scale by culturing shoot apexes of trees of genus Gmelina on a B5 medium or its modified medium, each containing benzylaminopurine (BAP) or indole-3-butyric acid (IBA) together with BAP as plant growth regulators, thereby inducing and proliferating multiple shoots each having a large number of either definite buds or adventitious buds or both, then producing a large number of shoots from the resulting multiple shoots, transplanting the shoots to a B5 medium or its modified medium containing no plant growth regulator or containing both BAP and IBA as plant growth regulators; and the regenerated plantlets can be efficiently acclimatized to outdoor conditions by transplanting the regenerated plantlets to a mixture of river sands and crushed brick pieces in a mixing ratio of 1:1 by volume and acclimatizing the transplanted plantlets to outdoor conditions in an acclimatization box; and in this manner, trees of genus Gmelina can be propagated on a large scale.

9 Claims, 5 Drawing Sheets

METHOD FOR LARGE-SCALE PROPAGATION OF TREES OF GENUS GMELINA BY TISSUE CULTURE

FIELD OF THE INVENTION

The present invention relates to a method for large-scale propagation of trees of the genus Gmelina, particularly, *Gmelina arborea* $R_{OXB}$ by tissue culture.

BACKGROUND OF THE INVENTION

Trees of the genus Gmelina are major afforested trees in tropical zones of the world, such as India and Southeast Asia Gmelina are also fast-growing trees whose woods are used for architectural materials, sculptural materials, pulps, fiberboards, plywoods, among other applications and whose barks, roots and fruits are used for medicines. Recent progress of plant tissue culture technique has enabled preservation of excellent varieties of many trees by tissue culture as genetic resources. Utilization of plant tissue culture technique has been expected for preservation, among other purposes of excellent varieties even of trees of the genus Gmelina. Generally, conventional techniques, such as afforestation by culturings, are not acceptable in attempts to propagate useful old trees. It is also understood that propagation of old trees is hard to conduct.

Recently, several research groups have been studying tissue culture techniques applied to trees of genus Gmelina to solve the problems so far encountered. In this connection, only two successful results have been reported up to now: J. C. Yang, G. Y. Tsay, J. D. Chung and Z. Z. Chon: Micropropagation of *Gmelina arborea* R. in Procedings of the SABRAO international symposium 29:213–218 (1992) and Crizald, E. N: Tissue culture of fast-growing trees in Sylvatrop 5(2); 123–137 (1980).

However, in these studies young plants germinated under aseptic conditions were used as materials. Thus regeneration and large-scale propagation of young plants from materials excised from mature trees containing a large amount of phenolic substances were not successfully carried out. Thus, development of an efficient propagation method using mature trees has been keenly desired.

SUMMARY OF THE INVENTION

An object of the present invention is to provide a large-scale propagation method that which enables large-scale production of trees of the genus Gmelina, particularly cloned nursery stocks of *Gmelina arborea* $R_{OXB}$.

As a result of extensive studies on development of large-scale propagation methods using nursery stocks or mature trees of the genus Gmelina, the present invention succeeded in induction of multiple shoots each having a large number of either definite buds or adventitious buds or both by culturing shoot apexes of trees of genus Gmelina, and successive efficient proliferation of multiple shoots. It was found that addition of benzylaminopurine (BAP) or indole-3-butyric acid (IBA) together with BAP to a medium for inducing multiple shoots and a medium for proliferating multiple shoots particularly could induce and proliferate multiple shoots efficiently, and also could promote shoot elongation efficiently from the proliferated multiple shoots. Furthermore, it was found that culturing of proliferated shoots in a medium containing no plant growth regulator or containing BAP or IBA together with BAP enabled further shoot elongation and rooting. Furthermore, it was found that when the plants thus generated were made to grow in an acclimatization box, preferably transplanted to a bed of river sands or crushed brick pieces or a mixture of river sands and crushed brick pieces as soils and made to grow in an acclimatization box with a spread layer of crushed brick pieces therein, acclimatization to outdoor conditions could be readily attained.

The present invention has been made on the basis of these findings.

According to a first aspect of the present invention, a method for large-scale propagation of trees of genus Gmelina comprises culturing shoot apexes of trees of the genus Gmelina, thereby inducing and proliferating multiple shoots each having a large number of either indefinite buds or adventitious buds or both. The method further produces a large number of shoots from the multiple shoots. The method also includes transplanting the shoots in a rooting medium, thereby regenerating plantlets.

According to a second aspect of the present invention, the method of the first aspect further comprises using a B5 medium or a modified B5 medium, each containing 0.01 to 0.3 mg/l of benzylaminopurine (BAP) or 0.002 to 0.02 mg/l of indole-3-butyric acid (IBA) together with 0.01 to 0.3 mg/l of BAP as plant growth regulators for a medium for culturing shoot apexes of trees of the genus Gmelina, thereby inducing and proliferating multiple shoots each having a large number of either definite buds or adventitious buds or both and further producing a large number of shoots from each of the multiple shoots.

According to a third aspect of the present invention, the method of the first aspect further comprises using a B5 medium or a modified B5 medium, each containing no plant growth regulator or containing 0.002 to 0.02 mg/l of IBA together with 0.01 to 0.3 mg/l of BAP as plant growth regulators for the rooting medium.

According to a fourth aspect of the present invention, the method of the first aspect further comprises using shoot apexes of nursery stocks or mature trees of the genus Gmelina.

According to a fifth aspect of the present invention, the method of the first aspect further comprises the trees of the genus Gmelina, being trees of *Gmelina.arborea* $R_{OXB}$.

According to a sixth aspect of the present invention, a method for large-scale propagation of trees of the genus Gmelina comprises culturing shoot apexes of trees of the genus Gmelina, thereby inducing and proliferating multiple shoots each having a large number of either definite buds or adventitious buds or both. A large number of shoots are produced from each of the multiple shoots. Then, individual shoots are translplanted to a rooting medium, thereby regenerating plantlets from the transplanted individual shoots. The making the regenerated plantlets are made to grow in a acclimatization box, thereby acclimatizing the plantlets to outdoor conditions.

According to a seventh aspect of the invention, the method of the sixth aspect further comprises the regenerated plantlets being transplanted to a bed of river sands, porous and hygroscopic mineral materials or a mixture of river sand and porous and hygroscopic mineral materials as soils and acclimatized.

According to an eighth aspect of the invention, the method of the sixth aspect further comprises the regenerated plantlets being transplanted to pots each containing river sands, porous and hygroscopic mineral materials or a mixture of river sands and porous and hygroscopic mineral materials as soils. The pots are placed in a closed acclimatization box provided with a spread layer of the mineral materials therein. The transplanted plants are then made to grow and acclimatized therein.

According to a ninth aspect of the present invention, the method of the sixth aspect further comprises the regenerated plantlets being acclimatized in an atmosphere at a temperature of 22° to 30° C. and a relative humidity of 80 to 90% with an illuminance of 5,000 to 10,000 Lux.

DETAILED DESCRIPTION OF THE INVENTION

Figure 1:
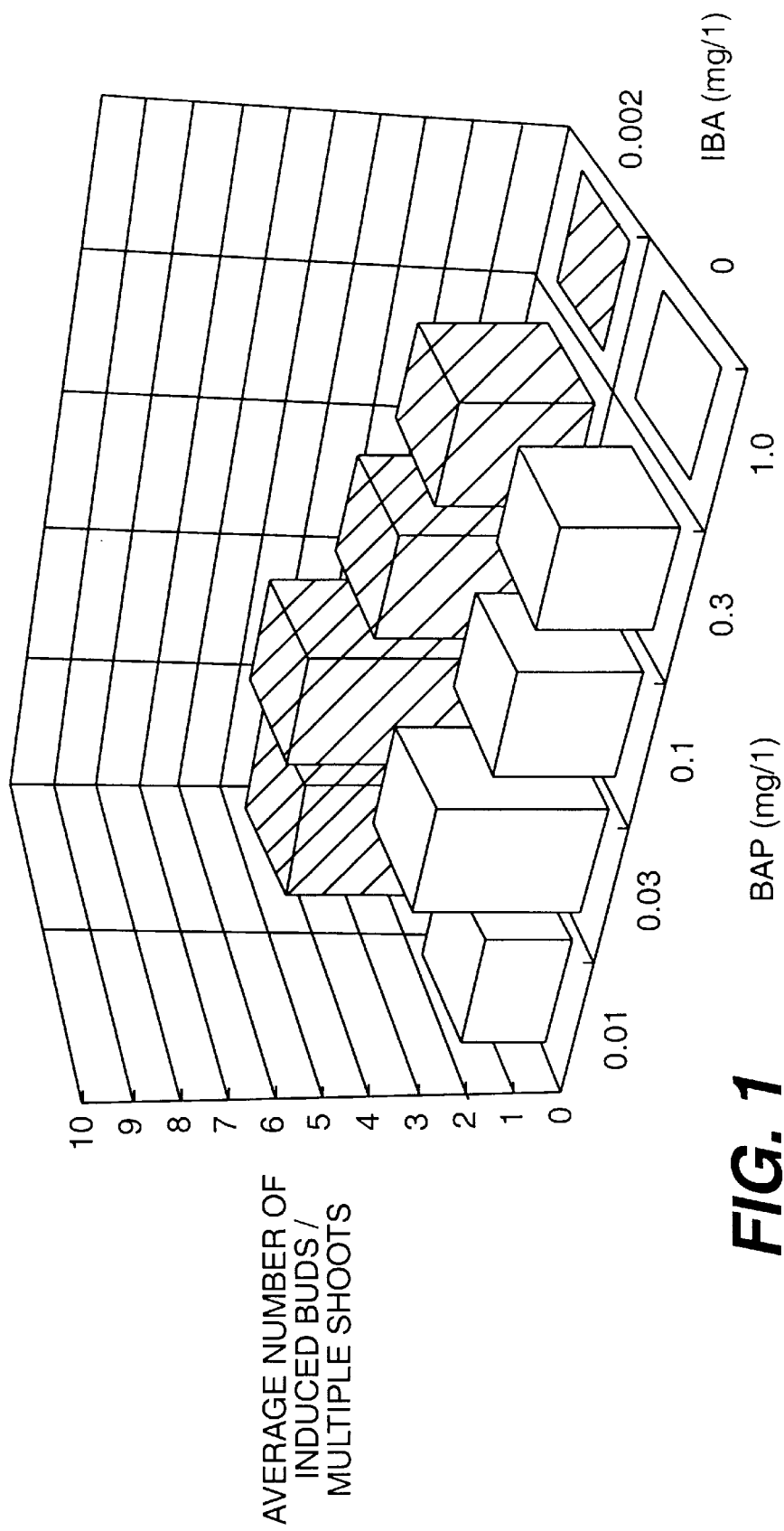
FIG. 1 is a diagram showing effects of IBA and BAP concentrations on induction of multiple shoots from nursery stock material.

According to the present invention, a large number of plantlets can be efficiently produced by inducing and proliferating multiple shoots from shoot apexes of nursery stocks and mature trees of the genus Gmelina, and then elongating and rooting individual shoots cut from the multiple shoots.

Trees of the genus Gmelina for use in the present invention can be exemplified by Gmelina arborea $R_{OXB}$.

Explant in the present invention is shoot apexes excised from nursery stocks and mature trees of the genus Gmelina. The excised shoot apexes are subjected to surface sterilization according to the ordinary method, using ethanol and sodium hypochlorite, hydrogen peroxide solution, or mercuric chloride (corrosive sublimate), followed by washing with sterilized distilled water and culturing on a medium.

Basal medium for use in culturing is a medium containing an inorganic substance and a carbon source as essential components and further containing a plant growth regulator, a vitamin and amino acids. The inorganic substance includes inorganic compounds including an element or elements such as nitrogen, phosphorus, potassium, sodium, calcium, sulfur, iron, manganese, zinc, iodine, boron, molybdenum, chlorine, cobalt, among others. The carbon source includes, for example, carbohydrates such as sucrose and glucose. The plant growth regulator includes, for example, auxin such as indole-3-butyric acid (IBA), α-naphthalene acetic acid (NAA), among others and cytokinin, such as benzylaminopurine (BAP), kinetin, zeatin, 4-phenylurea (4PU), among others. The vitamin includes, for example, thiamine, pyridoxine, nicotinic acid, among others. The amino acid includes, for example, glycine, glutamic acid, lysine, among others.

The medium for use in the actual culture is a medium usually used for plant tissue culture, such as MS medium [Murashige, T.: Physiol. Plant. 15: 473–497 (1962)], B5 medium [Gamborg, O. L.: Exp. Cell. Res. 50: 151–158 (1968)], WP medium [Lloyd, G.; Int. Plant Prop. Soc. 30: 421–427 (1981)], BTM medium [Chalupa, V.: Biologia Plnt. (Praha) 26: 374–377 (1984)], among others. Particularly preferable are the B5 medium and its modified medium. To induce and grow either definite buds or adventitious buds or both and promotes shoot growth from multiple shoots, it is preferable to use a B5 medium or its modified medium, each containing 0.01 to 0.3 mg/l of BAP, or 0.002 to 0.02 mg/l, preferably about 0.002 mg/l of IBA together with 0.01 to 0.3 mg/l of BAP as plant growth regulators.

Culturing is usually carried out at room temperature, more specifically at 20° C. to 30° C., preferably 25° C., in a clean room by solid culture, liquid gyratory culture, liquid rotary culture, among other techniques. Solid culture is particularly preferable.

Then, the elongated shoots from multiple shoots by shoot apex culture are cut into single shoots and transplanted to a rooting medium or directly transplanted thereto without cutting, whereby the single shoots or the elongated shoots can be further elongated and rooted.

A preferable rooting medium for use in the present invention is a medium containing the above-mentioned inorganic substance, carbon source, vitamin, amino acid, etc. without the plant growth regulator or with 0.01 to 0.3 mg/l of BAP and 0.002 to 0.02 mg/l, preferably about 0.002 mg/l of IBA as plant growth regulators.

According to one preferable embodiment of the present method for large-scale propagation of trees of the genus Gmelina by tissue culture, shoot apexes were first excised from mature trees of Gmelina arborea $R_{OXB}$, and cultured on a modified B5 medium containing 0.002 mg/l of IBA and 0.01 to 0.3 mg/l of BAP to induce and proliferate multiple shoots each having either definite buds or adventitious buds or both. Then a large number shoots were further produced from the multiple shoots. Then, the resulting shoots were transplanted to a rooting medium, which is a modified B5 medium containing 0.01 to 0.3 mg/l of BAP and 0.02 mg/l of IBA as plant growth regulators to induce rooting and efficient regeneration of plantlets.

The resulting regenerated plantlets are then made to grow in an acclimatization box to acclimatize the plantlets to outdoor conditions. Acclimatization of the regenerated plantlets is preferably carried out by transplanting the plantlets to a bed of soils of river sands, porous and hygroscopic mineral materials or a mixture of river sands and porous and hygroscopic mineral materials transplanted plantlets are made to grow in a closed acclimatization box at suitably controlled luminance, temperature and relative humidity. The porous and hygroscopic mineral materials include crushed brick pieces, pumice stone, kanuma soils, red roll soil and perlight. Crushed brick pieces are particularly preferable. Typically, river sands, porous and hygroscopic mineral materials or a mixture of river sands and porous and hygroscopic mineral materials are filled into pots as soils and the plantlets are transplanted to the soils in the pots. Preferably, the river sands have grain sizes of 0.5 to 3 mm and the mineral materials have sizes of 0.5 to 2 cm. The mixture of river sands and mineral materials as soils is preferably provided in a ratio of 1:1 by volume. Typically crushed brick pieces are crushed sun-dried brick pieces. Soils for transplanting plantlets for acclimatization can contain materials usually used for plant growth such as rice husks, large sawdusts, fallen tree pieces, gambut (fern roots), or mixtures of these materials.

Figure 5:
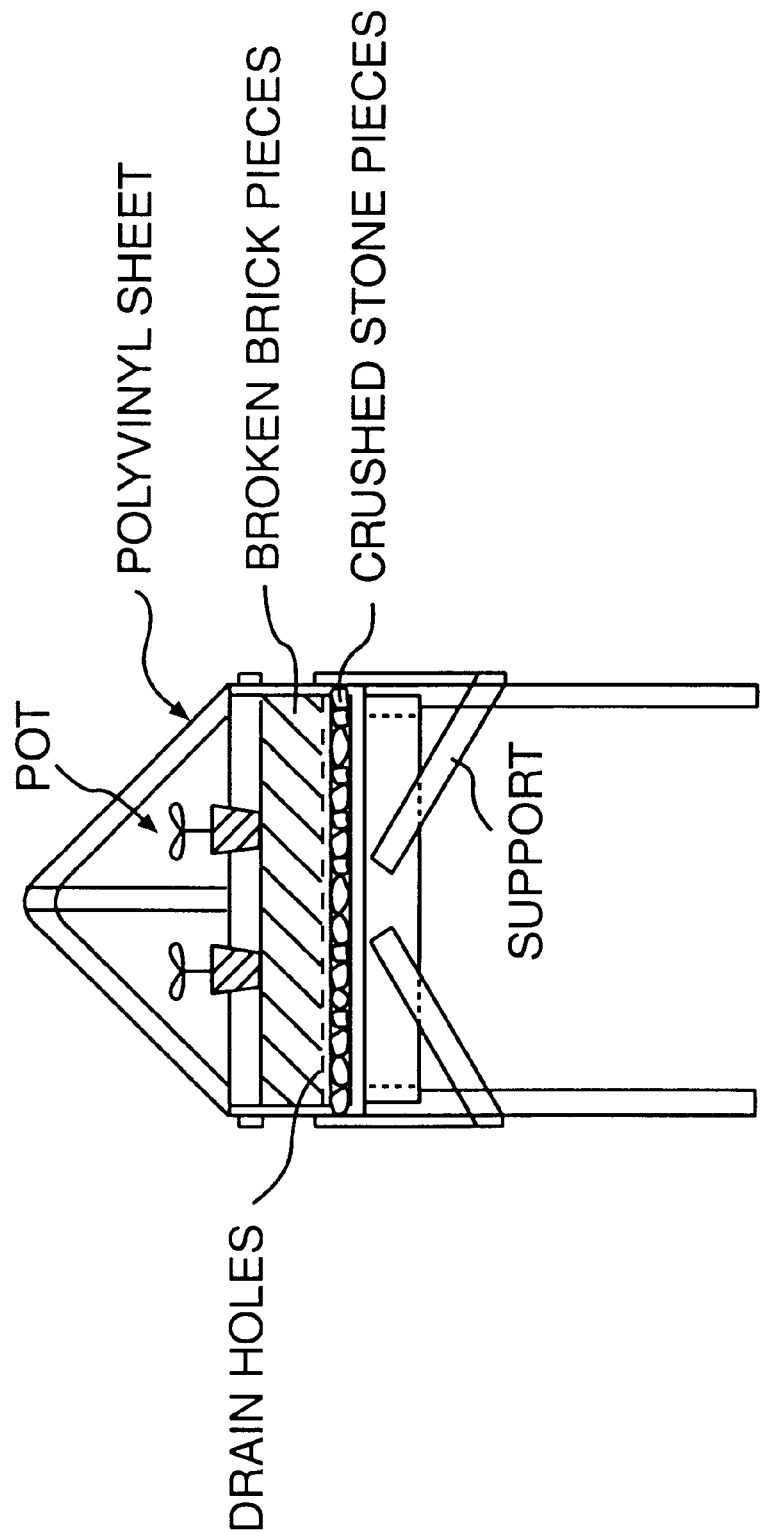
FIG. 5 is a cross-sectional view of one preferable embodiment of an acclimatization box for use in the present invention.

A typical acclimatization box is a housing made from wood, concrete, bricks, among other materials. The top of the box top is tightly closed with a water-impermeable material sheet such as a polyvinyl sheet. The inside bottom of the box is provided with a spread layer of soils with good drainage, such as porous and hygroscopic mineral materials, as shown in FIG. 5.

To control exposure of the plantlets to sunlight in the acclimatization box, it is preferable to cover the acclimatization box with shading materials, such a non-woven fabric, woven fabric, net (i.e., cheesecloth), vinyl sheet, plant bark, plant leaf, among other materials.

Acclimatization of plantlets in the acclimatization box is preferably carried out in an atmosphere such as a temperature of 22° to 30° C. and a relative humidity of 80 to 90% at a light intensity of 5,000 to 10,000 Lux. Particularly, a light intensity of 5,000 to 70,000 Lux is preferable. Acclimatization is usually continued for one week to two months.

According to the present invention, aseptic plantlets, and cuttings of trees of the genus Gmelina can be produced on a large scale for a short time in test tubes from materials excised from nursery stocks or mature trees of the genus Gmelina and can be efficiently acclimatized to outdoor conditions. That is, a large scale production of nursery stocks of trees of the genus Gmelina can be carried out.

PREFERRED EMBODIMENTS OF THE INVENTION

The present invention will be described in detail below, referring to the following Example.

EXAMPLE

Materials were excised from nursery stocks (0.2 to 0.5 m high) and mature trees (6.0 to 10.0 m high) of *Gmelina arborea* $R_{OXa}$.

(1) Sterilization of materials

Terminal buds were excised from nursery stocks and mature trees of *Gmelina arborea* $R_{OXa}$ and subjected to surface sterilization in 70% ethanol for 30 seconds and then in 2% sodium hypochlorite for 6 minutes, then to several washings with sterilized distilled water and then to air drying on a sterile filter paper. After the air drying, leaf primordia were removed from the terminal buds under an dissecting microscope to excise shoot apexes. The excised shoot apexes were cultured on an agar medium. As a result, the viability was found a little better in the case of the material excised from the nursery stocks than in the case of the material from the mature trees, but both materials excised from the nursery stocks and mature trees could be used in the present method.

Viability and withering rate of shoot apexes excised from the nursery stocks and mature trees are shown as comparative data in Table 1.

TABLE 1

| Materials | Viability and withering rate of excised materials | | |
|---|---|---|---|
| | Viability (%) | Withering rates (%) | Contamination rates (%) |
| Shoot apexes (from mature tree) | 70 | 10 | 20 |
| Shoot apexes (from nursery stacks) | 86 | 10 | 4 |

(2) Induction and proliferation of multiple shoots and shoot elongation

A medium was prepared by adding 20 g/l of sucrose, 3.4 g/l of gerlite, and 0.02 mg/l of IBA and 0.01 to 0.3 mg/l of BAP as plant growth regulators to a modified B5 medium, (which was a B5 medium including one-half amounts of all the components). The pH was adjusted to 5.7, followed by autoclaving.

Figure 3:
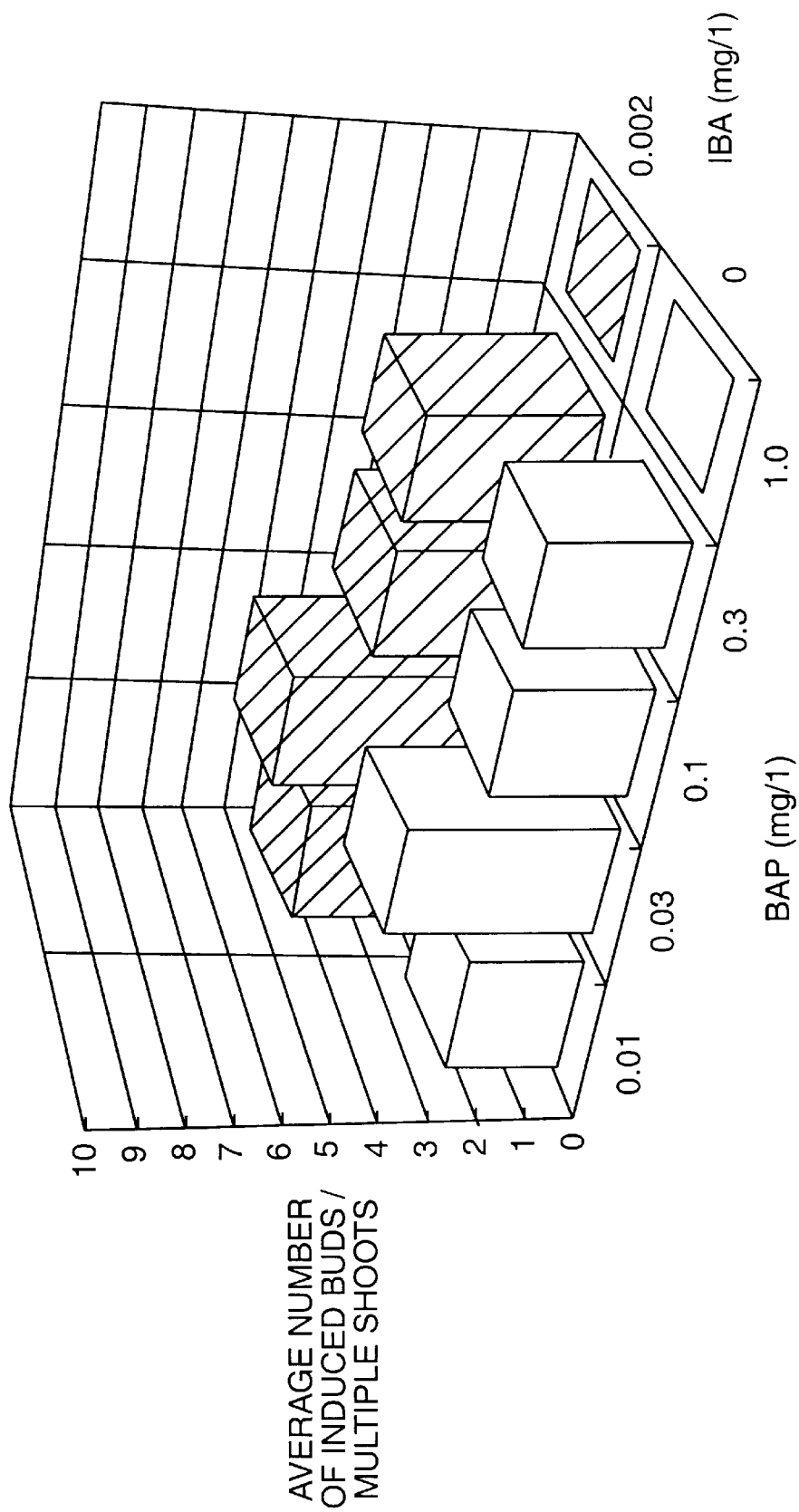
FIG. 3 is a diagram showing effects of IBA and BAP concentrations on induction of multiple shoots from mature tree material.

The sterilized materials obtained in Step (1) were cultured at a temperature of 26±2° C. under the illumination of cool white fluorescent tubes of 3,000 to 5,000 Lux for 16 hours per day. Two or three months after the start of culturing shoot apexes and multiple shoots were induced. Particularly, addition of 0.002 mg/l of IBA and 0.03 mg/l of BAP was found effective. Additionally no remarkable difference was found between the induction and proliferation of multiple shoots and shoot elongation between the materials used, as shown in FIGS. 1 and 3.

(3) Rooting

Figure 2:
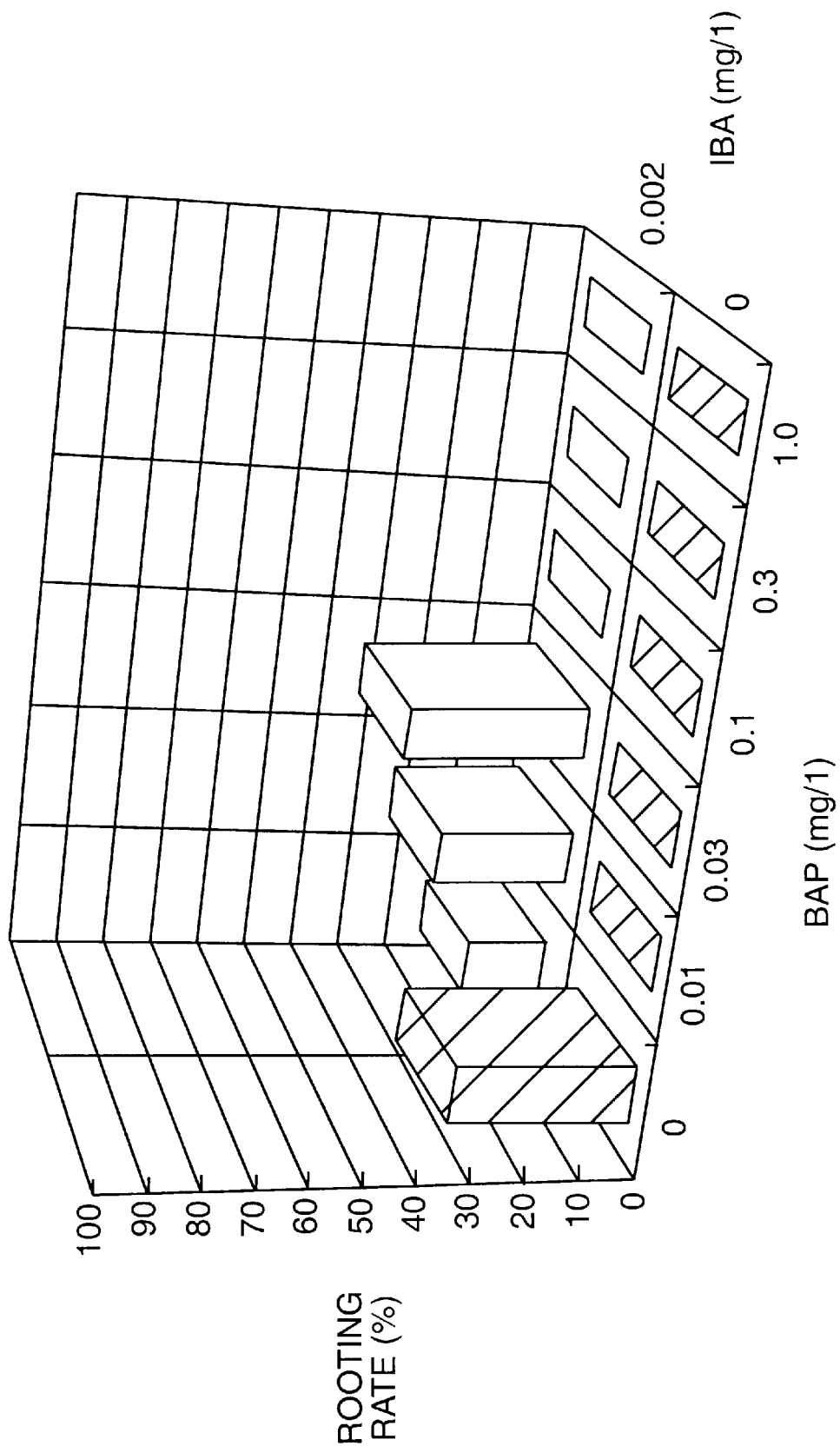
FIG. 2 is a diagram showing effects of IBA and BAP concentrations on rooting from nursery stock material.
Figure 4:
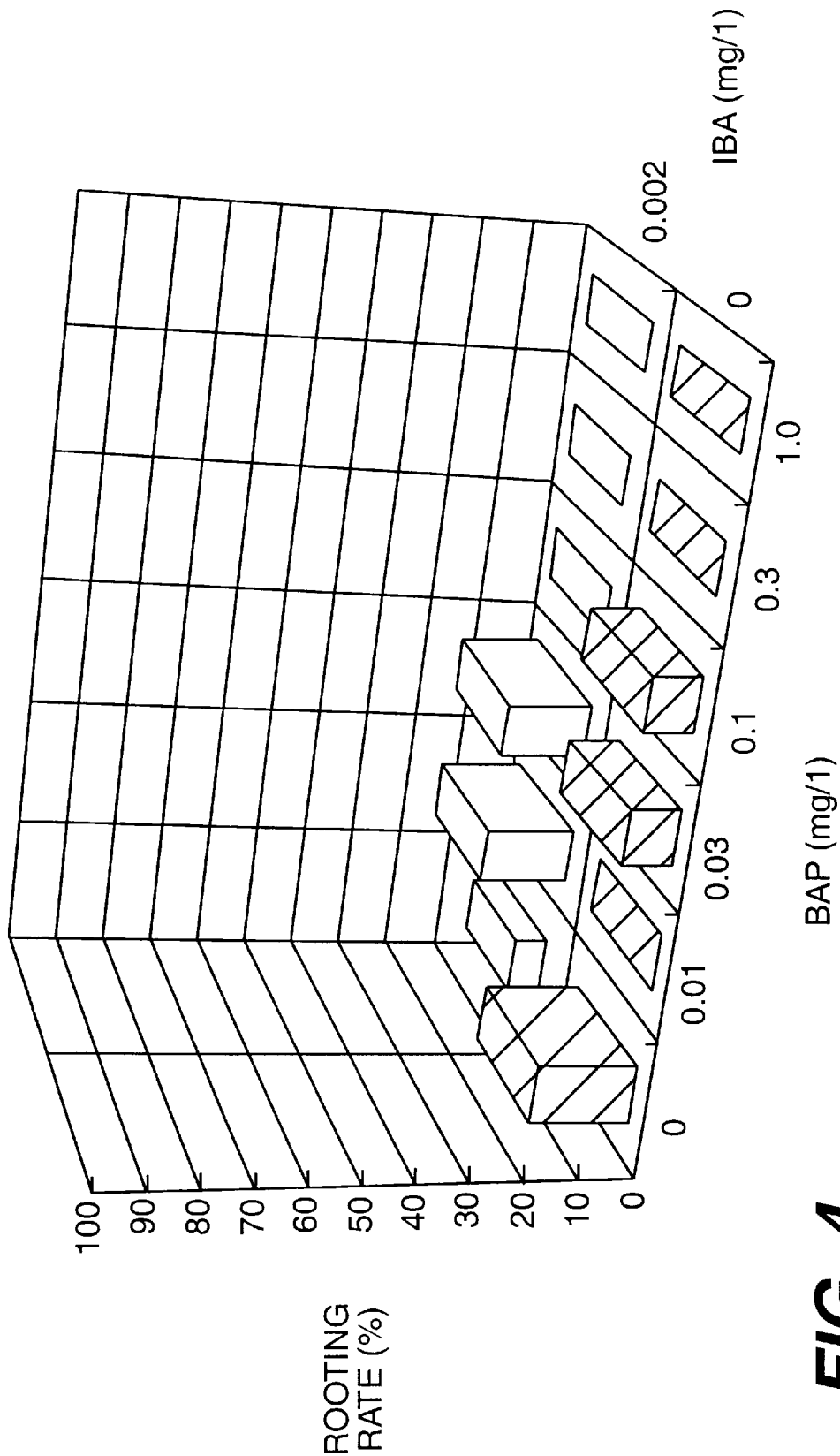
FIG. 4 is a diagram showing effects of IBA and BAP concentrations on rooting from mature tree material.

A large number of multiple shoots as obtained in Step (2) were cut into single shoots, and the single shoots were transplanted to rooting media in test tubes. The rooting media for use in this test included a modified B5 medium containing no plant growth regulators and a modified B5 medium containing 0.01 to 0.3 mg/l of BAP and 0.002 mg/l of IBA as plant growth regulators [the same as used in (2)]. Both media had been adjusted to pH 5.7 and sterilized before culturing. The transplanted shoots were cultured at a culturing temperature of 26±2° C. under the illumination of cool white fluorescence tubes of 3,000 to 5,000 Lux for 16 hours per day. One to two months after the start of culturing, rooting was observed for 33.3% of the individuals. At the same time, the shoots were elongated to 3–10 cm in length and 2 to 8 new leaves were developed. The medium containing no plant growth regulators and the medium containing 0.01 to 0.03 mg/l of BAP and 0.002 mg/l of IBA as plant growth regulator were found effective and there was found no remarkable difference in rooting between the materials used, as shown in FIGS. 2 and 4.

(4) Acclimatization

The plantlets obtained in Step (3) were taken out of the test tube, and the rooting media attached to the roots and stems were washed away therefrom with water. Then, the washed plantlets were transplanted to pots containing soils for acclimatization. The soils for use in this test included river sands having grain sizes of 0.5 to 3 mm, crushed brick pieces having sizes of 0.5 to 2 cm, and a mixture of the river sands and the crushed brick pieces in a mixing ratio of 1:1 by volume. All the soils were heat sterilized before the test. The transplanted plantlets in the pots were made to grow in an acclimatization box placed in a greenhouse for one month. The acclimatization box was in a wooden structure, as shown in FIG. 5. The box had dimensions such as 72 cm in bottom level height from the ground, 85 cm width and 4 m length. The box was provided with a 10-cm thick spread layer of crushed brick pieces on the inside bottom surface. A water-impermeable polyvinyl sheet was laid on the spread layer to maintain proper moisture inside the box. The water-permeable sheet further covered the top of the box to maintain proper moisture inside the box. The polyvinyl sheet laid on the spread layer of crushed brick pieces was provided with through holes, 1 cm in diameter, at spacings of 10 cm for water drainage. The interior of the acclimatization box was controlled to have an atmosphere such as a temperature of 22° to 30° C. and a relative humidity of 80 to 90% at an illuminance of 5,000 Lux, using cheesecloth.

It was found that the best results were obtained with the mixture of river sands and crushed brick pieces as soils.

Comparative data of viability, average of growth and withering rate of the plantlets due to differences in the kinds of soils used for acclimatization are shown in Table 2.

TABLE 2

Viability, average of growth and withering
rate of plant bodies due to differences in
kinds of soils used for acclimatization

| Soils | Viability (%) | Average of growth (cm) | Withering rates (%) |
|---|---|---|---|
| River sands | 71 | 2.4 | 29 |
| Crushed brick pieces | 67 | 1.3 | 33 |
| River sands crushed brick pieces | 80 | 5.0 | 20 |

To show the effect of using the acclimatization box, a control test was carried out by transplanting the plantlets to pots containing the mixture of the river sands and the crushed brick pieces in a mixing ratio of 1:1 by volume, and made to grow not in the acclimatization box but in a nursery bed under cheesecloth for one month to compare the viability and withering rate. The nursery bed was controlled to such a state of a temperature of 24° to 32° C. and a relative humidity of 50 to 80% at an illuminance of 8,000 to 40,000 Lux, using the cheesecloth.

One month after the start of the growth test, it was found that the plantlets made to grow in the acclimatization box showed normal growth, whereas all the plantlets made to grow in the nursery bed under the cheesecloth died by withering except one. The terminal bud of the only surviving plantlet was withered and fell off, showing no normal growth.

Comparative data of viability and withering rate of plantlets made to grow in the acclimatization box and in the nursery bed are shown in Table 3.

TABLE 3

Viability, average of growth and withering
rate of plant bodies made to grow in the
acclimatization box and in the nursery bed

| Growth site | Viability (%) | Average of growth (cm) | Withering rates (%) |
|---|---|---|---|
| Acclimatization box | 80 | 5.0 | 20 |
| Nursery bed | 20 | 0.7 | 80 |

What is claim is:

1. A method for large-scale propagation of trees of the genus Gmelina, which comprises the steps of:

culturing shoot apexes of trees of the genus Gmelina in a B5 medium or a modified B5 medium, said medium including 0.01 to 0.3 mg/l of benzylaminopurine or 0.002 to 0.02 mg/l of indole-3-butyric acid together with 0.01 to 0.3 mg/l of benzylaminopurine as plant growth regulators, thereby inducing and proliferating multiple shoots each having a large number of either definite buds or adventitious buds or both, and further producing a large number of shoots from each of the multiple shoots; and transplanting the shoots into a rooting medium including a B5 medium or a modified B5 medium, said rooting medium including no plant growth regulator or 0.002 to 0.02 mg/l of indole-3-butyric acid together with 0.01 to 0.3 mg/l of benzylaminopurine as plant growth regulators, thereby regenerating plantlets from the transplanted shoots.

2. A method according to claim 1, wherein the shoot apexes are those of nursery stocks or mature trees of genus Gmelina.

3. A method according to claim 1, wherein the trees of genus Gmelina are trees of *Gmelina arborea* $R_{OXB}$.

4. A method for large-scale propagation of trees of the genus Gmelina, which comprises the steps of:

culturing shoot apexes of trees of the genus Gmelina in a B5 medium or a modified B5 medium, said medium including 0.01 to 0.3 mg/l of benzylaminopurine or 0.002 to 0.02 mg/l of indole-3-butyric acid together with 0.01 to 0.3 mg/l of benzylaminopurine as plant growth regulators, thereby inducing and proliferating multiple shoots each having a large number of either definite buds or adventitious buds or both, and further producing a large number of shoots from each of the multiple shoots;

transplanting the shoots into a rooting medium including a B5 medium or a modified B5 medium, said rooting medium including no plant growth regulator or 0.002 to 0.02 mg/l of indole-3-butyric acid together with 0.01 to 0.3 mg/l of benzylaminopurine as plant growth regulators, thereby regenerating plantlets from the transplanted shoots; and growing the regenerated plantlets in an acclimatization box containing as soils a mixture of crushed brick pieces including at least one component selected from river sands and porous and hygroscopic mineral materials, thereby acclimatizing the plantlets to outdoor conditions.

5. A method according to claim 4, wherein the regenerated plantlets are transplanted to a bed of a mixture of crushed brick pieces with river sands.

6. A method according to claim 4, wherein the regenerated plantlets are acclimatized in an atmosphere at a temperature of 22° to 30° C. and a relative humidity of 80 to 90% at an illuminance of 5,000 to 10,000 Lux.

7. A method according to claim 5, wherein the shoot apexes are those of nursery stocks or mature trees of genus Gmelina.

8. A method according to claim 5, wherein the trees of genus Gmelina are trees of *Gmelina arborea* $R_{OXB}$.

9. A method according to claim 4, further comprising the steps of:

transplanting the regenerated plantlets to pots containing crushed brick pieces and river sands;

placing the pots in a closed acclimatization box provided with a spread layer of crushed brick pieces and river sands; and growing and acclimatizing the transplanted plantlets in the acclimatization box.

* * * * *